United States Patent [19]
Vetter et al.

[11] Patent Number: 5,346,822
[45] Date of Patent: Sep. 13, 1994

[54] **ALKALINE PROTEASES FROM *BACILLUS PUMILUS***

[75] Inventors: Roman Vetter, Burgdorf; Detlef Wilke, Wennigsen; Bernhard Moeller; Martina Mueller, both of Hannover; Ingo Muecke, Barsinghausen; Meike Takenberg, Hannover; Gerhard Konieczny-Janda, Pattensen, all of Fed. Rep. of Germany

[73] Assignee: Solvay Enzymes GmbH & Co. KG, Nienburg/Weser, Fed. Rep. of Germany

[21] Appl. No.: 67,086

[22] Filed: May 26, 1993

[30] Foreign Application Priority Data

Jun. 4, 1992 [DE] Fed. Rep. of Germany ....... 4218448

[51] Int. Cl.$^5$ ............................................... C12N 9/54
[52] U.S. Cl. ..................................... 435/221; 435/832
[58] Field of Search ..................... 435/221, 264, 832

[56] References Cited

U.S. PATENT DOCUMENTS

| | | | |
|---|---|---|---|
| 3,871,963 | 3/1975 | Tobe et al. | 435/221 |
| 3,905,869 | 9/1975 | Hidaka et al. | 435/221 |
| 4,771,003 | 9/1988 | Stellwag et al. | 435/221 |

OTHER PUBLICATIONS

T. Maniatis et al., Molecular Cloning, A Laboratory Manual, Cold Spring Marbor Laboratory (1982), pp. 93–95, 132–135, 146.
Anagnostopoulos et al., J. Bacteriol. 81, 746–791 (1961).
Bergey's Manual of Systematic Bacteriology, vol. 2, (1986), pp. 1121–1125.
T. J. Gyczan et al., J. Bacteriol. 134, 318–329 (1978).
Saito et al., Biochim. Biophys. Acta 72, 619–629 (1963).
S. Chang et al., Mol. Gen. Genet. 168, 111–115 (1979).
Biosis Previews Database Abstract No. 92009219: abstract of Qiu et al., Acta Microbiol. Sin., 30(6):445–49 (1990).
Biosis Previews Database Abstract No. 62060151: abstract of Acta Microbiol. Sin., 15(4):330–334 (1975).
Derwent WPI Abstract No. 86-112132: abstract of SU 1,183,538A.
Biosis Previews Database Abstract No. 91015259: abstract of Qiu et al., Acta Microbiol. Sin., 30(2):129–133 (1990).
Derwent WPI Abstract No. 89-160751: abstract of JP 1,101,886A.
Okotore et al., Z. Allgem. Mikrobiologie, vol. 21, No. 7, pp. 531–536 (1981).
Derwent WPI Abstract No. 91-307004: abstract of JP 3,205,499A.
Fabian, J.; Folia Microbiologica 15:169–175 (1970).
Qiu, et al.; Acta Microbiol. Sinica 24:66–73 (1984).

*Primary Examiner*—Robert A. Wax
*Assistant Examiner*—Eric Grimes
*Attorney, Agent, or Firm*—Evenson, McKeown, Edwards & Lenahan

[57] ABSTRACT

Alkaline Bacillus proteases, their use and a method for producing these proteases are described. These are in particular Bacillus proteases from *Bacillus pumilus* DSM 5777. The alkaline proteases according to the invention are suitable for use in compositions for cleaning and washing purposes.

8 Claims, 6 Drawing Sheets

ALKALINE PROTEASES FROM *BACILLUS PUMILUS*

BACKGROUND OF THE INVENTION

The present invention relates to alkaline proteases from *Bacillus pumilus*, to their use and to a method for producing these proteases.

Alkaline proteases are valuable industrial products with advantageous applications, in particular in the detergent industry, since they remove protein-containing contaminants. In order to be effective, these proteases must not only have proteolytic activity under washing conditions (pH value, temperature), but they must also be compatible with other detergent constituents, e.g. other enzymes, surfactants, builders, bleaching agents, bleaching agent activators and other additives and adjuvants. In particular, the proteases must possess sufficient stability with respect to these detergent constituents and sufficient washing effectiveness in their presence.

The alkaline proteases of the prior art have been obtained in particular by cultivation of Bacillus species, such as *Bacillus alcalophilus, Bacillus subtilis, Bacillus amyloliquefaciens* and *Bacillus licheniformis*, which produce alkaline proteases and secrete them into the culture medium.

Many attempts have already been made in the prior art to obtain new alkaline proteases having desired properties. For instance, a series of natural and artificially (genetically) altered alkaline and highly alkaline proteases is already known. However, there remains a need for new, alkaline proteases having beneficial properties, particularly with respect to their washing behavior.

SUMMARY OF THE INVENTION

It is the object of the invention to provide new alkaline proteases having advantageous properties.

Another object of the invention is to provide alkaline proteases which are compatible with other ingredients of washing and detergent compositions.

A further object of the invention is to provide alkaline proteases which exhibit good washing effectiveness.

These and other objects of the invention are achieved by providing an alkaline Bacillus protease having a pH optimum in the pH range of about pH 8.0 to 11.5 and a temperature optimum in the range of about 50° to 60° C., obtainable by cultivation of *Bacillus pumilus* DSM 5777 or a microorganism transformed to contain in expressible form a highly alkaline protease gene isolatable from *Bacillus pumilus* DSM 5777.

DETAILED DESCRIPTION OF PREFERRED EMBODIMENTS

Surprisingly, it has been found that alkaline Bacillus proteases which can be obtained by cultivation of *Bacillus pumilus* DSM 5777 or of a transformed microorganism which contains the genetic information for one of these proteases possess advantageous properties with a pH optimum in the alkaline pH range of about pH 8.0 to 11.5 and with a temperature optimum in the range of about 50° to 60° C. and demonstrate very good washing effectiveness.

Advantageously, the alkaline proteases according to the invention have amino acid sequences which have at least 70%, preferably over 80%, and particularly preferably over 90%, homology (sequence correspondence) with the amino acid sequences of the proteases from *Bacillus pumilus* DSM 5777. "Homology" is understood in this case to be a very close relationship between the relevant amino acid sequences of the proteases according to the invention and the amino acid sequences of the proteases from *Bacillus pumilus* DSM 5777. In order to determine the homology, in each case the sections which correspond to one another of the amino acid sequence of the proteases from *Bacillus pumilus* DSM 5777 and an amino acid sequence of a protease which is to be compared with it are made to coincide with each other such that there is maximum correspondence between the amino acid sequences, with differences caused by deletion or insertion of individual amino acids being taken into consideration and being compensated for by corresponding displacements of sequence sections. The number of the amino acids which then match one another in the sequences ("homologous positions"), relative to the total number of the amino acids contained in the sequence of one of the proteases from *Bacillus pumilus* DSM 5777, gives the homology in %. Deviations in the sequences may be caused by variation, insertion and/or deletion of amino acids.

The proteases according to the invention are obtainable by cultivation of *Bacillus pumilus* DSM 5777 or by cultivation of a transformed Bacillus microorganism which contains the genetic information for one of the proteases according to the invention from *Bacillus pumilus* DSM 5777, e.g. in an expression vector.

Analysis of the culture supernatant from a culture of *Bacillus pumilus* DSM 5777 with the aid of HPLC (=high pressure liquid chromatography) shows that at least two proteases having differing properties can be obtained from *Bacillus pumilus* DSM 5777.

One of the preferred proteases according to the invention from *Bacillus pumilus* DSM 5777 is an alkaline Bacillus protease having the following properties:
(1) Action: degradation of proteins and peptides;
(2) pH optimum: approximately at pH values of 10.5 to 11.0;
(3) pH stability: at pH values of 9.7 to 10.8, the enzymes prove to be completely stable;
(4) temperature optimum: approximately 60° C.;
(5) temperature stability: activity of the protease not significantly impaired by incubation at temperatures of up to 45° C. for 15 minutes; residual activity of the protease is at least 90% after 15 minutes' incubation at 50° C.;

The other one of the preferred proteases according to the invention from *Bacillus pumilus* DSM 5777 has the following properties:
(1) Action: degradation of proteins and peptides;
(2) pH optimum: approximately at pH values of 8.5 to 9;
(3) pH stability: at pH values of 5.5 to 10.5, the enzymes prove to be completely stable;
(4) temperature optimum: approximately 50° C.;
(5) temperature stability: activity of the protease not significantly impaired by incubation at temperatures of up to 40° C. for 15 minutes; residual activity of the protease is at least 95% after 15 minutes' incubation at about 45° C.;

The Bacillus proteases according to the invention are useful as additives for detergent and cleaning agent compositions etc. which have neutral to alkaline pH values and are intended to be used at low temperatures, in particular at temperatures of up to 60° C. The invention therefore also relates to the use of the alkaline Bacillus proteases according to the invention in detergent, cleaning agent or dishwashing agent compositions. They may also advantageously be used in the presence of other conventional enzymes, in particular in the presence of other proteases. A particularly preferred use of the alkaline proteases according to the invention relates to their use in detergent, cleaning agent or dishwashing agent compositions for low use temperatures, in particular of up to about 60° C., preferably for use temperatures of about 30° to 60° C.

Furthermore, the invention relates to detergent, cleaning agent and dishwashing agent compositions which contain at least one of the alkaline proteases according to the invention. For these applications, the invention provides a group of novel alkaline proteases having beneficial properties, by means of which protein-containing soiling can advantageously be removed. Both soiling containing egg yolk and soiling containing blood and milk are removed equally well. No significant impairment of the washing effectiveness of the proteases according to the invention by the other constituents contained in the detergent formulations can be detected in washing tests.

The proteases according to the invention may be used in detergent and cleaning agent formulations, for instance in powdered detergent formulations, individually or if desired in combination, optionally also in combination with detergent and cleaning agent proteases of the prior art or other enzymes which are conventional in such compositions, such as proteases, amylases, lipases, pectinases, nucleases, oxido-reductases, cellulases etc. The proteases according to the invention are used in the detergent and cleaning agent formulations in quantities which are usual for detergent enzymes, in particular in quantities of up to 3% by weight (relative to the dry mass of the overall composition), preferably in a quantity of 0.2 to 1.5% by weight).

In addition to the detergent enzymes already mentioned, the detergents and cleaning agents of the invention may contain all the detergent constituents which are conventional in the prior art, such as surfactants, bleaching agents or builders, and also additional conventional adjuvants for detergent formulations in conventional quantities. Examples of adjuvants include intensifiers, enzyme stabilizers, anti-redeposition agents and/or compatibility agents, complexing and chelating agents, foam regulators and additives such as optical brighteners, opacifying agents, corrosion inhibitors, anti-electrostatic agents, dyes, bactericides, bleaching agent activators, and/or peracid bleaching agent precursors.

Thus, by way of example, a typical detergent composition formulation according to the invention may contain, relative to dry substance,
 a) at least 5% by weight, e.g. 10 to 50% by weight, of a surfactant or surfactant mixture,
 b) up to 40% by weight of a builder or builder mixture,
 c) up to 40% by weight of a bleaching agent or bleaching agent mixture, preferably a perborate such as sodium perborate tetrahydrate or sodium perborate monohydrate,
 d) up to 3% by weight of at least one protease according to the invention, and
 e) additional constituents such as adjuvants, etc., to make up to 100% by weight.

Such detergent formulations may be formulated in conventional manner. The proteases according to the invention may additionally be mixed with the other constituents of the detergent formulation in a known manner, for instance in the form of granules, prills or pellets, which may optionally also provided with surface coatings.

Furthermore, the proteases according to the invention are also highly suitable for use in conventional liquid detergent formulations.

The alkaline proteases according to the invention may be obtained by cultivating *Bacillus pumilus* DSM 5777 or a microorganism containing the genetic information for one of the proteases according to the invention and subsequently isolating the resulting alkaline protease from the culture supernatant. The isolation of the alkaline proteases from the culture supernatant is carried out in known manner, in that the cells are separated by filtration or centrifugation, the protease is concentrated by membrane filtration or precipitation, purified, optionally isolated, and dispatched to its intended use.

For example, the *Bacillus pumilus* strain DSM 5777 itself or a transformed *Bacillus pumilus* strain which contains the genetic information for one of the proteases according to the invention, e.g. in an expression vector, can be used for producing and obtaining the proteases according to the invention.

For large-scale production, particularly in order to simplify and optimize production and to increase the yield, other microorganisms, especially Bacillus strains, into which the necessary genetic information for the proteases according to the invention and the expression thereof has previously been introduced by transformation, may also be used for producing and obtaining the proteases according to the invention.

The invention therefore also comprises a method for producing the alkaline proteases according to the invention with transformed microorganisms which contain an expression vector with DNA sequences which are required for protease expression and with a DNA sequence which codes for an amino acid sequence of one of the above-described alkaline proteases according to the invention. The microorganism transformed according to the invention is cultivated as stated above, and the alkaline protease is isolated from the culture medium. Preferred transformed microorganisms for producing and obtaining the protease according to the invention are Bacillus species such as *Bacillus subtilis, Bacillus alcalophilus, Bacillus licheniformis* or *Bacillus amyloliquefaciens*. The microorganisms transformed according to the invention are distinguished in particular in that they are transformed with an expression vector which contains the genetic information for an alkaline protease from *Bacillus pumilus* which was deposited on Feb. 9, 1990 under the number DSM 5777 in the Deutsche Sammlung von Mikroorganismen (German Collection of Microorganisms). Likewise, the invention therefore also comprises the microorganisms deposited on Feb. 23, 1992 under the numbers DSM 6879 and DSM 6880, and also the plasmids which can be isolated from these microorganisms and which contain the genetic information for the above-described proteases according to the invention.

In order to produce the transformed microorganisms used in the above process, which are also covered by the invention, one can proceed in that a) first the DNA sequence which codes for the protease (i.e. the structural gene of the protease) is isolated from a suitable bacteria strain which produces an alkaline protease with an amino acid sequence having at least 70%, preferably over 80%, particularly preferably over 90%, homology to the amino acid sequence of the protease from *Bacillus pumilus* DSM 5777;

b) optionally the nucleotide sequence of this DNA sequence is determined in order further to identify the protease;

c) subsequently, an expression vector is produced using the isolated DNA sequence and d) the resulting expression vector is transformed into a suitable microorganism which can finally be used for the production of the alkaline protease.

The process steps for isolating and obtaining the alkaline proteases according to the invention using the above process, and also the intermediate products obtained thereby, in the form of DNA sequences or DNA inserts with the protease gene, vectors, in particular expression vectors, and transformed microorganisms, which are in part likewise a subject of the invention, will be described individually in greater detail below.

The structural genes which code for the amino acid sequences of the alkaline proteases according to the invention may be obtained using known general methods. To this end, the chromosomal DNA is isolated, for instance from *Bacillus pumilus* DSM 5777 ("donor Bacillus"), using known methods, and is partially hydrolysed with suitable restriction endonucleases.

The resulting restriction fragments of the donor DNA can be separated according to size by a sucrose density gradient gel centrifugation or electrophoresis and the fragments of desired size can then be recombined with a suitable vector DNA. Advantageously, a plasmid with which the foreign DNA introduced into the host organism can be expressed is used as a vector. As described in the examples, for example a plasmid having the designation pUB131, which has been produced by introducing a polylinker site into the plasmid pUB110, may be used.

The DNA obtained above, which is recombined in vitro, can then be introduced into suitable host cells, e.g. into the strain *Bacillus subtilis* PSL1 used here. Transformants, i.e. host cells which have taken up the recombinant DNA, may be selected with the aid of known markers on the vector DNA (e.g. neomycin resistance). Of these antibiotic-resistant transformants, those clones which express increased amounts of protease can be selected. Of such transformants, those which are capable of expressing a protease according to the invention may be isolated. Finally, the plasmid DNA introduced into this transformant may be isolated from a positive clone using known techniques.

In addition to the vector DNA with known restriction sites, this plasmid contains the desired structural gene for the alkaline protease from *Bacillus pumilus* DSM 5777 according to the invention and optionally additional DNA sequences from the donor Bacillus which are, however, not required for the present invention. Examples of such protease-containing plasmids include the plasmids having the designations pPP46 and pPP415. The plasmid pPP46 has a size of 7.6 kilobases and codes for the protease P46 according to the invention from *Bacillus pumilus* DSM 5777. The plasmid pPP415 has a size of 6.2 kilobases and codes for the protease P415 according to the invention from *Bacillus pumilus* DSM 5777.

The ability of these plasmids to express the corresponding alkaline protease can be tested by transforming a bacterium, in particular a Bacillus species of the type mentioned above, with one of these plasmids, cultivating the resulting transformants, and testing them for protease activity. The resulting transformants may furthermore also be cultivated for producing and obtaining the alkaline proteases according to the invention, in which case the alkaline proteases according to the invention described above are obtained.

The proteases according to the invention from *Bacillus pumilus* DSM 5777 are distinguished by advantageous properties. At alkaline pH values, they have a high stability. The pH optimum of the proteases according to the invention lies in a range of approximately pH 8.0 to 11.5, which is advantageous for use in detergent and cleaning agent compositions. Furthermore, the proteases according to the invention have a temperature optimum in the range of about 50° to 60° C. They have good stability, even in washing solutions. Due to their beneficial activity at temperatures of up to 60° C., the Bacillus proteases according to the invention are particularly suitable for use in cleaning agent and detergent compositions which are intended to be used at low temperatures, in particular up to 60° C., preferably between 30° and 60° C. Such detergent and cleaning agent compositions which contain a protease according to the invention demonstrate beneficial washing effectiveness with respect to protein stains which are to be removed.

The following examples illustrate the invention in a typical configuration by way of example, but without restricting the scope of the invention. Unless otherwise indicated, procedures were generally carried out in accordance with the methods described in Maniatis et al. (Maniatis et al.=T. Maniatis, E. F. Fritsch, J. Sambrook, "Molecular Cloning, A Laboratory Manual", Cold Spring Harbor Laboratory, 1982). The various restriction endonucleases used are known in the art and are commercially available. The reaction conditions, cofactor conditions and other conditions required when using these known restriction endonucleases are also known. For example, for a quantity of approximately 1 $\mu$g DNA one unit (=1 U=unit) of the restriction endonuclease in approximately 20 $\mu$l of a buffer solution may be used. Sufficient incubation times of about one hour at 37° C. were usually maintained, but the incubation conditions may be adapted to the existing requirements. After incubation with a restriction endonuclease, the protein was removed by extraction (e.g. with phenol and chloroform) and the cut DNA (e.g. from the aqueous fraction by precipitation with ethanol) was isolated and sent for further use.

Optionally hydrolysis of the terminal 5'-phosphate group with an alkaline phosphatase (dephosphorylation) may follow the restriction of DNA or vectors with restriction endonucleases. When dephosphorylation of the 5'-end was performed in the examples, this took place in known manner. Further details of the dephosphorylation procedure and reagents required therefor can be obtained from Maniatis et al. (pp. 133–134).

Partial hydrolysis means incomplete digestion of DNA by a restriction endonuclease. The reaction conditions are chosen such that cuts are made in a DNA substrate at some, but not at all, the recognition sites for the restriction endonuclease used.

In order to obtain and isolate certain DNA fragments, e.g. after treatment of DNA with restriction endonucleases, the resulting DNA fragments were separated in a known manner by gel electrophoresis (e.g. on agarose gel), then identified by means of the molecular weight (determination by comparison with reference DNA fragments of known molecular weight), and the desired DNA fragment was recovered from the corresponding gel zone.

Ligations may be performed under known conditions, e.g. in a buffer with approximately 10 units T4-DNA-ligase per 0.5 μg of the DNA fragments which are to be ligated (see e.g. Maniatis et al., p. 146).

"Transformation" is understood to be the introduction of DNA into a microorganism so that the DNA can be replicated or expressed therein. For Bacillus species, for example, the method of Anagnostopolous et al. (1961, J. Bacteriol. 81:746-791) is suitable.

When enzyme stabilities are stated in the following examples, the term "completely stable" refers to a residual activity of at least 90%, and the term "stable" means a residual activity of at least 80%.

The *Bacillus pumilus* strain described in Example 1 was isolated from nature and deposited in the German Collection of Microorganisms (Deutsche Sammlung von Mikroorganismen und Zellkulturen GmbH in Braunschweig, Germany—DSM) under the number DSM 5777 on Feb. 7, 1990. The strain *B. subtilis* PSL1 transformed with the plasmid pPP46 given in Example 3 was deposited under the number DSM 6879 and the strain *B. subtilis* PSL1 transformed with the plasmid pPP415 given in Example 3 was deposited under the number DSM 6880 in the Deutsche Sammlung von Mikroorganismen und Zellkulturen GmbH on Jan. 22, 1992. Other microorganisms used, e.g. *Bacillus subtilis* PSL1 (Bacillus Genetic Stock Center 1 A 510) or Bacillus BD366 (Bacillus Genetic Stock Center 1 E 6) are commercially available.

BRIEF DESCRIPTION OF THE DRAWINGS

The invention will be described in further detail hereinafter with reference to the accompanying drawings wherein.

EXAMPLE 1

Isolation of a *Bacillus pumilus* from nature and the identification thereof

The strain *Bacillus pumilus* was isolated from nature and deposited in the German Collection of Microorganisms under the number DSM 5777. This is a Gram-positive, spore-forming aerobic microorganism of the genus Bacillus. The cell-morphological and colony-morphological description will be given below; biochemical reactions and reactions to certain growth conditions are listed in Table 1.

*Bacillus pumilus* DSM 5777

Rod-shaped bacterium with rounded ends. The Gram reaction (Gram staining, KOH test) is positive. On TY agar (see below), the colonies after 2 days at 37° C. have a diameter of 3.2 to 4.2 mm, are beige-colored and have a smooth to wavy edge. Occasionally droplet formation may also be observed on the colonies; the colonies may be lustrous or dried-up and wrinkled. The cells have a size of 0.8 to 0.9 μm*1.2 to 2.8 μm on TY agar and as a rule are present as individual cells or in chains of two or three. The spores are oval and centrally to sub-terminally located. The strain sporulates spontaneously.

TY agar:

| Yeast extract | 5 g |
| --- | --- |
| $MgCl_2*6H_2O$ | 8.75 g |
| $MnCl_2*2H_2O$ | 0.016 g |
| Agar | 16 g |
| Double distilled water | to make up to 1000 ml |
| pH | 7.0 ± 0.3 |

Based on the results obtained after performing the tests listed in Table 1 (in accordance with Bergey's Manual of Systematic Bacteriology, Vol. 2, 1121-1125, P.H.A. Sneath (ed.), Williams and Wilkins, Baltimore-London-Los AngelesSydney, 1986), the organism can be assigned to the species *Bacillus pumilus*. The isolated strain DSM 5777 deviates only in a few features (Voges-Proskauer test, pH of the V-P nutrient solution and formation of egg yolk-lecithinase, and also with respect to the growth at 7% NaCl) from the characteristics listed therein for *Bacillus pumilus*.

*Bacillus pumilus* is a ubiquitously-occurring organism which forms colonies of variable appearance on nutrient media.

TABLE 1*

| Feature | DSM 5777 | *Bacillus pumilus* |
| --- | --- | --- |
| Cell diameter >1 μm | − | − |
| Spore form round | − | − |
| Sporangium swollen | − | − |
| Parasporal crystals | − | − |
| Catalase | + | + |
| Anaerobic growth | − | − |
| Voges-Proskauer test | − | + |
| pH in V-P nutrient solution | | |
| <6 | | + |
| >7 | + | |

TABLE 1*-continued

| Feature | DSM 5777 | Bacillus pumilus |
|---|---|---|
| Acid formation on | | |
| glucose | + | + |
| L-arabinose | + | + |
| D-xylose | + | + |
| D-mannitol | + | + |
| Gas formation with glucose | − | − |
| Hydrolysis of | | |
| casein | + | + |
| gelatine | + | + |
| starch | − | − |
| Metabolization of | | |
| citrate | + | + |
| propionate | − | − |
| Degradation of tyrosine | − | − |
| Deamination of phenylalanine | − | − |
| Egg yolk-lecithinase | + | − |
| Nitrate reduction to nitrite | − | − |
| Formation of | | |
| indole | − | − |
| dihydroxyacetone | − | n.d. |
| NaCl or KCl requirement | n.d. | − |
| Allantoin or ureate requirement | n.d. | − |
| Growth at pH = | | |
| 6.8 in NB | + | + |
| 5.7 in NB | + | + |
| Growth in NaCl | | |
| 2% | n.d. | + |
| 5% | + | + |
| 7% | − | + |
| 10% | − | n.d. |
| Growth at | | |
| 5° C. | n.d. | − |
| 10° C. | n.d. | + |
| 30° C. | + | + |
| 40° C. | n.d. | + |
| 50° C. | n.d. | d |
| 55° C. | n.d. | − |
| 65° C. | n.d. | − |
| Growth in the presence of lysozymes | + | d |
| Autotrophic with $H_2 + CO_2$ or CO | n.d. | − |

*Particulars of B. pumilus according to Bergey's Manual of Systematic Bacteriology, Vol. 2, p. 1123, P. H. A. Sneath, ed., Williams and Wilkins, Baltimore-London-Los Angeles-Sydney, 1986.
+, 90% or more positive
−, 90% or more negative
d, 11–89% positive
n.d., not determined
NB, nutrient broth

EXAMPLE 2

Production of the plasmid pUB131

The plasmid pUB110 was isolated from the strain *Bacillus subtilis* BD366 (pUB110) (Bacillus Genetic Stock Center 1 E 6) according to the method of T. J. Gryczan et al. (1978, J. Bacteriol. 34: 318–329) and was then purified according to Maniatis et al. (p. 93) by means of caesium chloride density gradient centrifugation. The vector pUB110 contains restriction sites for the restriction endonucleases BamHI and EcoRI which occur only once and as a marker a DNA sequence which codes for antibiotic-resistance with respect to neomycin, and also DNA sequences required for replication in Bacillus species ("origin of replication").

The plasmid pUB110 obtained above was cleaved with EcoRI and BamHI, with a larger and a smaller fragment being obtained. The smaller fragment 790 bp (bp=base pairs) was replaced by a 67 bp polylinker, which had previously been isolated from the vector M13tg131 as an EcoRI/BglII fragment. The resulting vector, designated pUB131, is thus a derivative of pUB110 in which the EcoRI/BamHI fragment, which is approximately 0.8 kB in size, has been deleted and a polycloning site inserted in its place.

EXAMPLE 3

Cloning of the alkaline proteases P46 and P415 from *Bacillus pumilus* DSM 5777

The chromosomal DNA was isolated from the natural isolate *Bacillus pumilus* DSM 5777 of Example 1 in accordance with the method of Saito et al. (1963, Biochim. Biophys. Acta. 72, pages 619–629) and was partially hydrolyzed with the restriction endonuclease Sau3A. The restriction fragments were separated by electrophoresis on an agarose gel, and the fragments having a size of 3 to 8 kB (kB=kilobases) were isolated.

The isolated DNA fragments from the Bacillus DSM 5777 were recombined in vitro with vector DNA of the plasmid pUB131 (produced as described in Example 2). To this end, the plasmid pUB131 was first cleaved with the restriction endonuclease BamHI and then dephosphorylated with alkaline phosphatase from calf intestine. Then 4 μg of the cleaved and dephosphorylated vector DNA were incubated with 20 μg of the DNA fragments from the Bacillus DSM 5777 in a total volume of 200 μl with T4-DNA ligase for 24 hours at 16° C.

Protoplasts of the strain *Bacillus subtilis* PSL1 (Bacillus Genetic Stock Center 1 A 510) were transformed with the DNA recombined in vitro in accordance with the method described by S. Chang and N. Cohen (1979, Mol. Gen. Genet. 168, pages 111–115). The transformants were selected on plates with neomycin and then transferred to skimmed milk agar plates. Of approximately 100,000 neo$^r$-transformants obtained, several clones were found which could be identified as intensified protease excretors due to a clear halo around the respective colony.

These clones were cultivated in TY medium with 10 μg/ml neomycin (10 g tryptone, 5 g yeast extract, 4.1 mg $MgCl_2 \times 2H_2O$ and 16 mg $MnCl_2 \times 2H_2O$ made up to 1000 ml with aqua bidest.) for 24 hours. The proteases in the culture supernatants were separated on an HPLC column—Ultropak TSK CM-2SW, 250×4.6 mm (manufactured by LKB)—and were detected using UV light (280 mm). A linked flow-injection analysis (substrate: acetyl casein; detection reagent: trinitrobenzene sulfonic acid; detection at 420 nm) made it possible to differentiate the peaks with proteolytic activity from other protein peaks. In addition to clones which express increased amounts of only those proteases native to the host, some were found which in addition to the native proteases each also express a protease foreign to the host. Based on the elution times, two different proteases foreign to the host could be identified, which were designated as protease P46 and protease P415. The plasmids from these clones which express the proteases which can be found in the culture supernatant of *Bacillus pumilus* DSM 5777 and thus contain the genetic information of these proteases were designated as pPP46 and pPP415 respectively. The plasmid pPP46 had a size of 7.6 kB, and the plasmid pPP415 a size of 6.2 kB. The strain *B. subtilis* PSL1 transformed with the plasmid pPP46 was deposited on Jan. 22, 1992 in the Deutsche Sammlung von Mikroorganismen under the number DSM 6879. The strain *B. subtilis* PSL1 transformed with the plasmid pPP415 was deposited on Jan. 22, 1992 in the Deutsche Sammlung von Mikroorganismen under the number DSM 6880.

EXAMPLE 4

Production of the alkaline proteases P46 and P415 from *B. pumilus* DSM 5777

The plasmids pPP46 and pPP415 were isolated from the clones *B. subtilis* PSL1 (pPP46) and *B. subtilis* PSL1 (pPP415) of Example 3 and introduced into the donor strain *B. pumilus* DSM 5777. The transformation was effected as a protoplast transformation in accordance with the method of Chang and Cohen (see Example 2). Then 40 ml of preculture medium (10 g tryptone, 5 g yeast extract, 5 g NaCl, 10 mg neomycin, double distilled water to make up to 1000 ml) were inoculated in 500 ml shaking flasks with an individual colony of the strain *B. pumilus* DSM 5777 (pPP46) or of the strain *B. pumilus* DSM 5777 (pPP415) from an agar plate. The culture was incubated for 16 hours at 37° C. and 250 rpm. 40 ml of primary culture medium (40 g soya meal, 90 g potato starch, 1.5 g $Na_2SO_4$, 3.5 mg $MnCl_2$, 10 mg neomycin and double distilled water to make up to 1000 ml) were inoculated with 1 ml of this culture in 500 ml shaking flasks. The primary culture was incubated for 30 hours and at 320 rpm under conditions which were otherwise the same as for the preculture, and centrifuged after 30 hours.

The alkaline proteases could be purified from the supernatant by means of FPLC (CM Sepharose FF (Pharmacia) elution buffer 0.05M Na acetate pH 6 and 0.8M Na acetate pH 6) or the culture supernatant could be used directly for further experiments.

EXAMPLE 5

Determination of the enzyme characteristics of *Bacillus pumilus* proteases

The activity of the proteases was determined in Delft units (DU). 1000 DU is the proteolytic activity which yields an extinction difference (1 cm light path; 275 nm; determination against blank test) of 0.4000 for a volume of 1 ml of a 2% (w/w) enzyme solution after the digestion of casein.

The culture supernatants obtained in Example 4 by cultivation of the strains *Bacillus pumilus* DSM 5777 (pPP46) and DSM 5777 (pPP415) were used to determine the enzyme characteristics such as temperature optimum, temperature stability, pH optimum and pH stability.

Figure 1:
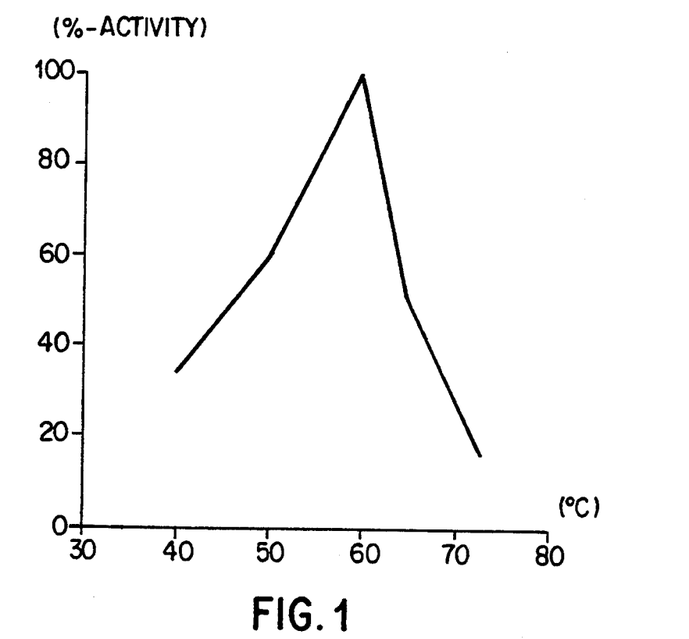
FIG. 1 is a graph showing the optimum temperature of protease P46 from *Bacillus pumilus* DSM 5777.
Figure 2:
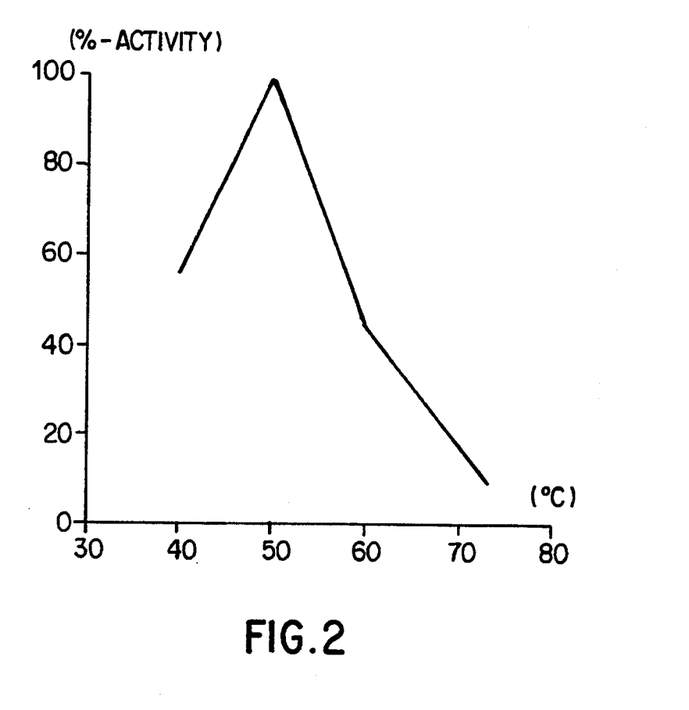
FIG. 2 is a graph showing the optimum temperature of protease P415 from *Bacillus pumilus* DSM 5777.

The temperature optimum of the proteases contained in the culture supernatants was determined in the range from 40° to 73° C. The results are illustrated in Table 2 and in FIGS. 1 and 2. The temperature optimum of the protease P46 from *Bacillus pumilus* DSM 5777 (pPP46) is 60° C. (FIG. 1). The temperature optimum of the protease P415 from *Bacillus pumilus* DSM 5777 (pPP415) is 50° C. (FIG. 2).

TABLE 2

Temperature optimum of the alkaline proteases from *Bacillus pumilus* DSM 5777 (pPP46) and DSM 5777 (pPP415)

| alkaline protease | activity in % as a function of the temperature in °C. | | | | |
|---|---|---|---|---|---|
| | 40° C. | 50° C. | 60° C. | 65° C. | 73° C. |
| P46 | 34% | 59% | 100% | 50% | 16% |
| P415 | 56% | 100% | 45% | 32% | 10% |

In order to determine the temperature stability, the protease-containing supernatants were incubated for 15 minutes at various temperatures and then the residual activity was determined. The results are listed in Table 3 and illustrated in FIGS. 3 and 4. The protease P46 from *Bacillus pumilus* DSM 5777 (pPP46) is stable at 50° C. (residual activity>90%), and still demonstrates a residual activity of 57.3% (FIG. 3) after 15 minutes incubation at 55° C. The protease P415 from *Bacillus pumilus* DSM 5777 (pPP415) is stable at 45° C. (residual activity>90%), and still demonstrates a residual activity of 76.4% (FIG. 4) after 15 minutes incubation at 50° C.

TABLE 3

Figure 3:
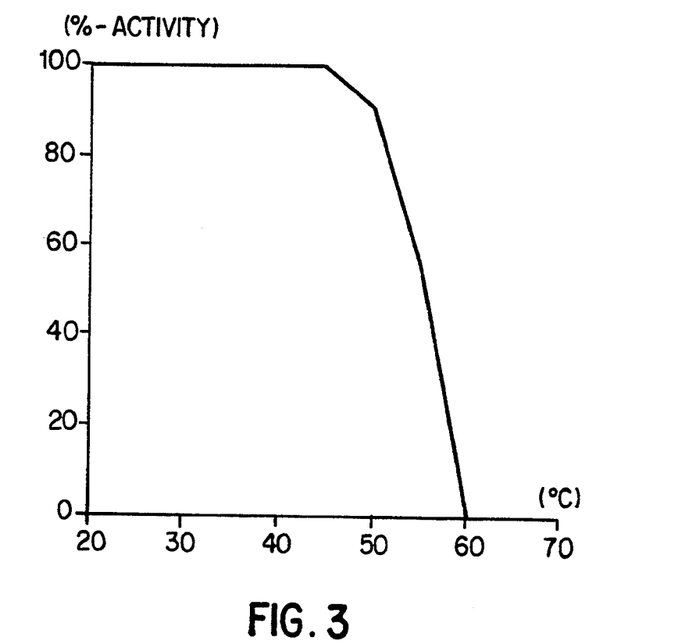
FIG. 3 is a graph showing the temperature stability of protease P46 from *Bacillus pumilus* DSM 5777.
Figure 4:
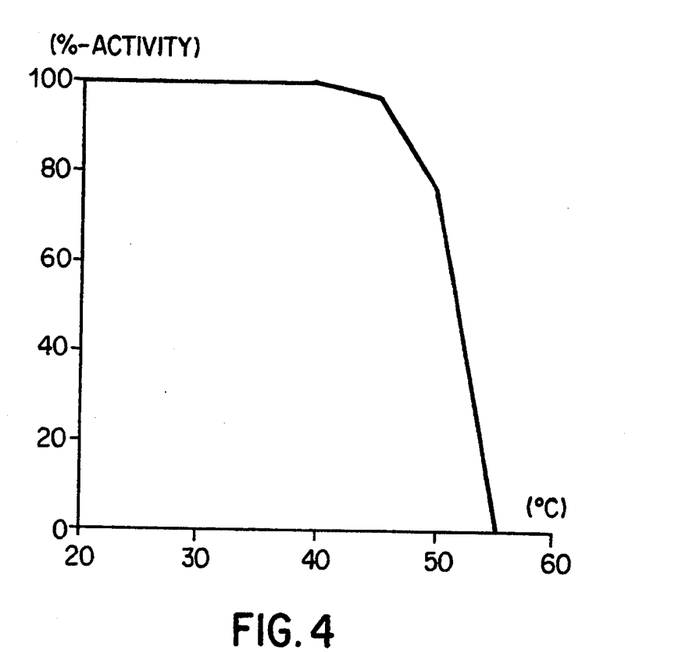
FIG. 4 is a graph showing the temperature stability of protease P415 from *Bacillus pumilus* DSM 5777.

| Temperature [°C.] | proteolytic residual activity in % after 15 minutes' incubation at various temperatures | |
|---|---|---|
| | P46 | P415 |
| 20 | 100 | 100 |
| 30 | 100 | 100 |
| 40 | 100 | 100 |
| 45 | 100 | 96.9 |
| 50 | 90.9 | 76.4 |
| 55 | 57.3 | 1.9 |
| 60 | 2.3 | <0.2 |
| 65 | <0.2 | <0.2 |

Figure 5:
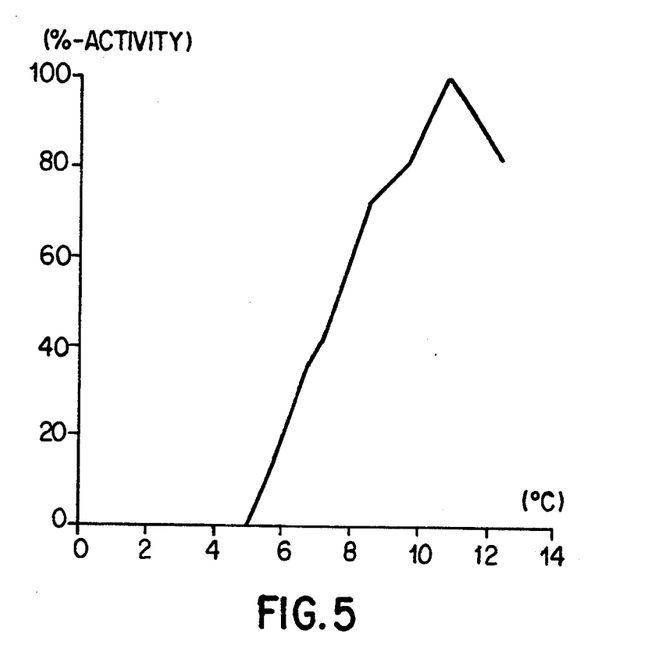
FIG. 5 is a graph showing the pH optimum of protease P46 from *Bacillus pumilus* DSM 5777.
Figure 6:
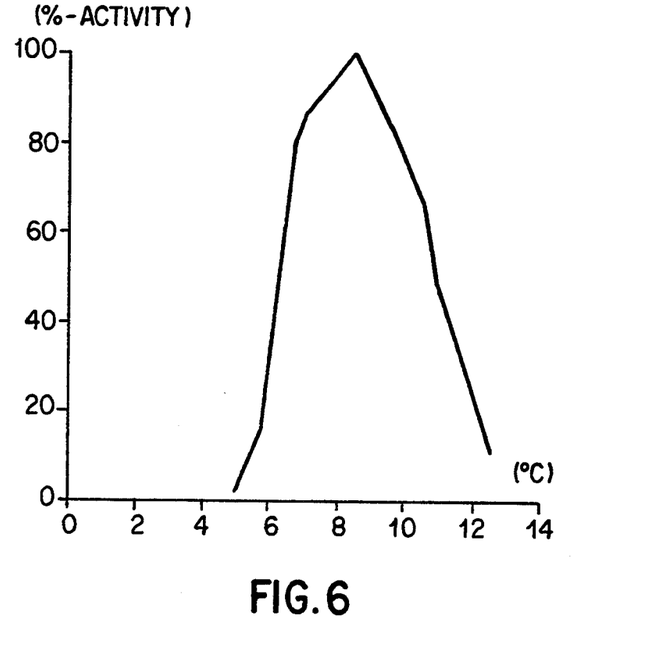
FIG. 6 is a graph showing the pH optimum of protease P415 from *Bacillus pumilus* DSM 5777.

In order to determine the pH optimums of the Bacillus proteases, the activity was determined for various pH values. To set the pH values, phosphate buffer (0.1M) was used in the pH range from pH 5 to pH 7, tris-HCl buffer (0.1M) was used in the pH range from pH 7.0 to pH 9.0, and glycine-NaOH buffer (0.1M) was used in the pH range from pH 9.0 to pH 13.0. The values from the activity determinations are listed in Table 4 and illustrated in FIGS. 5 and 6. The pH optimum of the alkaline protease P46 from *Bacillus pumilus* DSM 5777 (pPP46) is pH 10.9. At pH 12.5, the activity is still>80% (FIG. 5). The pH optimum of the alkaline protease P415 from *Bacillus pumilus* DSM 5777 (pPP415) is about pH 8.6 (FIG. 6).

TABLE 4

| alkaline protease | protease activity in % as a function of the pH value pH | | | | | | | | |
|---|---|---|---|---|---|---|---|---|---|
| | 5.0 | 5.8 | 6.8 | 7.2 | 8.6 | 9.8 | 10.6 | 10.9 | 12.5 |
| P46 | 0 | 14 | 36 | 41 | 72 | 82 | 95 | 100 | 81 |
| P415 | 2 | 16 | 79 | 87 | 100 | 81 | 65 | 50 | 10 |

Figure 7:
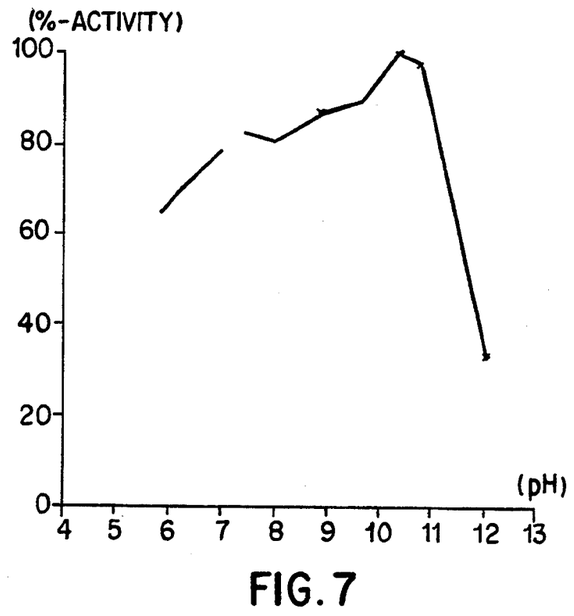
FIGS. 7 and 8 are graphs showing the pH stability of the proteases P46 (FIG. 7) and P415 (FIG. 8) from *Bacillus pumilus* DSM 5777; in order to set the pH value, 0.1M phosphate buffer was used for the pH range from pH 5 to pH 7; 0.1M tris-HCl buffer was used for the pH range from pH 7 to pH 9, and 0.2M glycine-NaOH buffer was used for the pH range from pH 9 to pH 12.1.
Figure 8:
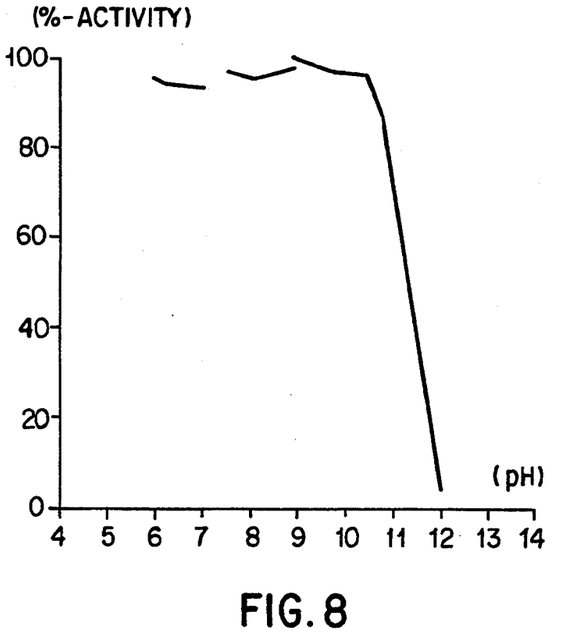

In order to investigate the pH stability, the proteases were incubated at 4° C. for 24 hours in buffers having different pH values. Then the residual activity of the proteases was determined. To set the pH values, phosphate buffer (0.1M) was used for the pH range from pH 5 to pH 7.1, tris-HCl buffer (tris(hydroxymethyl)aminomethane buffer) (0.1M) was used for the pH range from pH 7.1 to pH 9, and glycine-sodium hydroxide buffer (0.1M) for the pH range from pH 9 to pH 12.1. The results are illustrated in FIGS. 7 and 8. The protease P46 from *Bacillus pumilus* DSM 5777 (pPP46) is largely stable between pH 5.8 and 9.7, and completely stable between pH 9.7 and 10.8; 34% residual activity can still be detected after 24 hours at pH 12.06 (FIG. 7). The protease P415 *Bacillus pumilus* DSM 5777 (pPP415) is completely stable between pH 5.8 and 10.4, and largely stable between pH 10.4 and 10.8 (FIG. 8).

EXAMPLE 6

Washing efficiency of the protease P46

The effect of the protease P46 according to the invention was determined in washing tests.

EXAMPLE 6a

For use as a detergent additive, the washing efficiency of the protease according to the invention was determined by washing tests on test fabric EY-PC (egg yolk/India ink staining on polyester/cotton mixed fabric—own production) in laboratory washing machines (type: Polycolor). For this purpose the test fabric was washed with 6 g/liter of a detergent base formulation which contained 18.4% zeolite, 7.3% $Na_2CO_3$, 4.8% linear alkyl benzene sulphonate, 3.3% nonionics, 3.3% soap, 0.1% defoamer, 1.5% carboxymethylcellulose, 0.15% optical brighteners, 3.5% sodium disilicate, 25% perborate, 1.5% TAED (tetraacetyl ethylene diamine) and 30.85% $Na_2SO_4$, after the addition of the protease according to the invention (5,000 DU/l) in water of 15° dH. The washing solution had a pH of 10.3. Washing was carried out in a temperature range of 15° C. to 60° C. for 45 minutes (2° C./min; 22.5 min holding time).

The enzyme-containing detergent solution acted on the test fabric in a rotating test vessel which was regulated in accordance with the temperature program via a water bath. After the washing process, the test fabric was rinsed twice with tap water and then ironed.

The washing effectiveness was determined by measuring the reflectance of the washed test fabric. The washing effectiveness achieved by the enzyme is indicated by the higher reflectance of the test fabric washed with the enzyme-containing detergent. A reflectance value of 41 was determined for test fabric which was washed only with the base detergent formulation. When the protease P46 according to the invention was added to the detergent base formulation, a considerably higher reflectance value of 45 was found for the test fabric.

EXAMPLE 6b

The washing effectiveness of the protease P46 according to the invention was investigated as described in Example 6a. The detergent base formulation was a commercially available heavy-duty powder detergent (pH 10.4). The determination of the reflectance of the test fabric for the base detergent formulation yielded a value of 41. When the protease P46 according to the invention was added to the detergent base formulation, a considerably higher reflectance value of 48 was measured for the test fabric.

EXAMPLE 6c

The washing effectiveness of the protease P46 according to the invention was investigated as described in Example 6b, except that a polyester/cotton mixture (EMPA 117 obtained from the Federal Materials Testing Institute, St. Gallen, Switzerland) stained with blood, milk and India ink was used as the test fabric. 4 g/liter of a commercially available liquid detergent (pH 7.5) were used as the base detergent formulation. Washing was carried out in the temperature range of 15° C. to 40° C. (2° C./min; 22.5 min holding time).

Without the addition of the protease P46 according to the invention, the washed test fabric was determined to have a reflectance value of 50. When the protease P46 according to the invention was added, a value of 62 was determined for the reflectance of the washed test fabric.

EXAMPLE 6d

The washing effectiveness of the protease P46 according to the invention was investigated as described in Example 6c, except that a polyester/cotton mixed fabric stained with egg yolk and India ink was used as the test fabric. Without the addition of the protease P46, a reflectance value of 41 was measured for the washed test fabric. When the protease P46 according to the invention was added to the base detergent formulation, a value of 45 was measured.

EXAMPLE 6e

The washing effectiveness of the protease P46 according to the invention was investigated as described in Example 6d, except that a polyester/cotton mixed fabric stained with milk and India ink was used as the test fabric without the addition of the protease P46, a value of 45 was measured for the reflectance of the washed test fabric. When the protease P46 according to the invention was added to the base detergent formulation, a value of 52 was measured.

The results of Examples 6a to 6e demonstrate the outstanding washing efficiency of the protease P46 according to the invention. The reflectance of the washed test fabric is considerably higher when the protease according to the invention is added to the base detergent formulation, which is an indication of the good washing efficiency of the protease P46 according to the invention. Protein soiling of various kinds is outstandingly removed from the fabric by the protease P46.

EXAMPLE 7

Washing efficiency of the protease P415

The washing effectiveness of the protease P415 according to the invention was investigated as described in Example 6 for the protease P46.

EXAMPLE 7a

Figure 9:
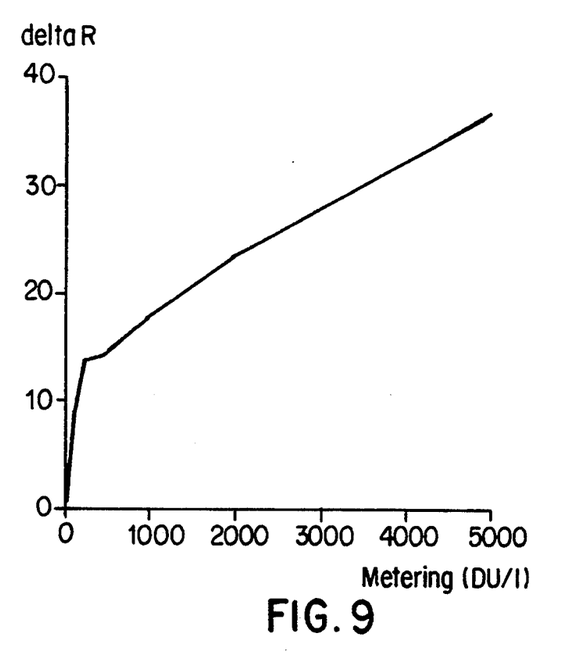
FIG. 9 is a graph showing the washing effectiveness of the protease P415 on test fabric M-PC as a function of the amount of enzyme used (delta R=difference in reflectance)
Figure 10:
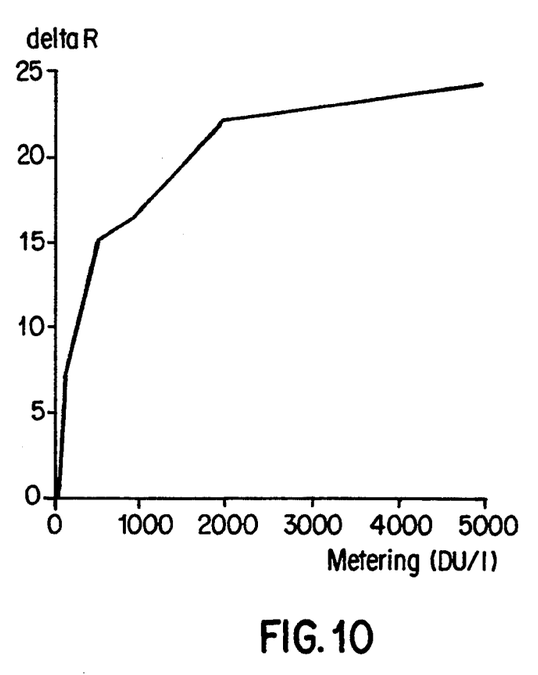
FIG. 10 is a graph showing the washing effectiveness of the protease P415 on test fabric Y-MC as a function of the amount of enzyme used (delta R=difference in reflectance)

The washing effectiveness as a function of the amount of enzyme used (DU/ml) was investigated on two different test fabrics (M-PC=milk/India ink stain on polyester/cotton mixed fabric; EY-PC=egg yolk-/India ink stain on polyester/cotton mixed fabric). A commercially available European liquid detergent was used as the base detergent formulation. The reflectance of the washed test fabric was determined as described in Example 6. The results of the washing tests are shown in FIG. 9 (M-PC) and FIG. 10 (EY-PC), in which the difference in reflectance between the test fabric washed with the addition of the protease P415 according to the invention and the test fabric washed without the addition of the protease P415 is plotted as a function of the amount of enzyme used.

EXAMPLE 7b

Figure 11:
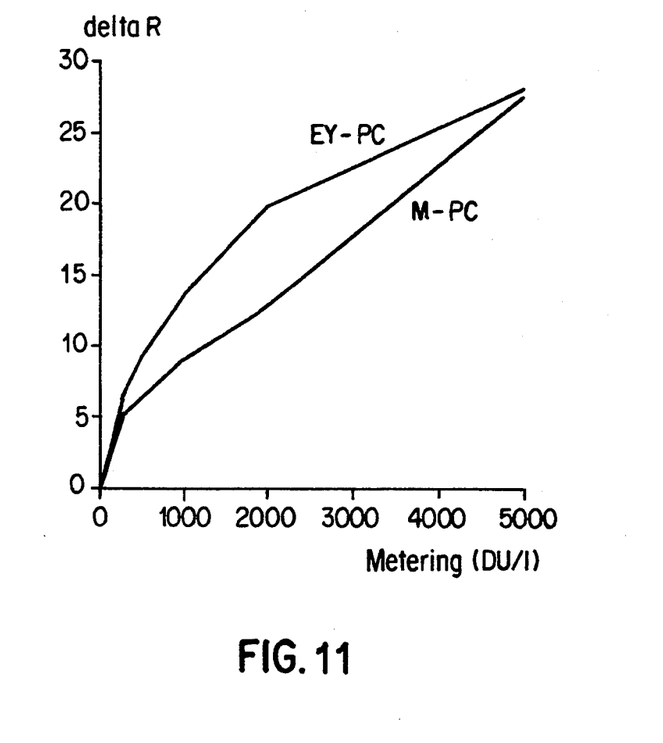
FIG. 11 is a graph showing the washing effectiveness of the protease P415 on test fabrics as a function of the amount of enzyme (delta R=difference in reflectance). reflection difference).

The washing effectiveness of the protease P415 according to the invention was investigated as described in Example 7a, except that a commercially available European compact detergent (pH 10.3) was used as base detergent formulation. The amount used was 3 g/liter. The results of the washing tests are shown in FIG. 11 as differences in reflectance as a function of the amount of enzyme used.

The results of Examples 7a and 7b demonstrate the outstanding washing effectiveness of the protease P415 according to the invention, with very good washing efficiency being achievable even when low amounts of enzyme are used. Protein soiling of various kinds is outstandingly removed from the fabric by the protease P415 during the washing process.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An isolated alkaline Bacillus protease obtained by cultivation of *Bacillus pumilus* DSM 5777 or a microorganism transformed to contain in expressible form a highly alkaline protease gene isolated from *Bacillus pumilus* DSM 5777, said protease having either set of the following properties:
   (1) Action: degradation of proteins and peptides;
   (2) pH optimum: approximately between pH values of 10.5 to 11.0:
   (3) pH stability: upon incubation at 4° C. for 24 hours at pH values between 9.7 to 10.8 the enzyme proves to be completely stable;
   (4) temperature optimum: approximately 60° C.;
   (5) temperature stability: by incubation of the protease at temperatures of up to 45° C. for 15 minutes. The activity of the protease is substantially 100%; after 15 minutes' incubation at 50° C., the residual activity of the protease is at least 90%;

or
   (1) Action: degradation of proteins and peptides;
   (2) pH optimum: approximately between pH values of 8.5 to 9.01;
   (3) pH stability: upon incubation at 4° C. for 24 hours between pH values of 5.5 to 10.5, the enzyme proves to be completely stable:
   (4) temperature optimum: approximately 50° C.;
   (5) temperature stability: by incubation of the protease at temperatures of up to 40° C. for 15 minutes, the activity of the protease is substantially 100%; after 15 minutes' incubation at 45° C., the residual activity of the protease is at least 95%. incubation at 45° C. the residual activity of the protease is at least 95%.

2. An isolated alkaline Bacillus protease according to claim 1, having the following properties:
   (1) Action: degradation of proteins and peptides;
   (2) pH optimum: approximately at pH values of 10.5 to 11.0;
   (3) pH stability: upon incubation at 4° C. for 24 hours at pH values of 9.7 to 10.8, the enzyme proves to be completely stable;
   (4) temperature optimum: approximately 60° C.;
   (5) temperature stability: by incubation of the protease at temperatures of up to 45° C. for 15 minutes, the activity of the protease is substantially 100%; after 15 minutes' incubation at 50° C., the residual activity of the protease is at least 90%.

3. An isolated alkaline Bacillus protease according to claim 1, having the following properties:
   (1) Action: degradation of proteins and peptides;
   (2) pH optimum: approximately at pH values of 8.5 to 9;
   (3) pH stability: upon incubation at 4° C. for 24 hours at pH values of 5.5 to 10.5, the enzyme proves to be completely stable;
   (4) temperature optimum: approximately 50° C.;
   (5) temperature stability: by incubation of the protease at temperatures of up to 40° C. for 15 minutes, the activity of the protease is substantially 100%; after 15 minutes' incubation at 45° C., the residual activity of the protease is at least 95%.

4. A composition for washing, cleaning or dishwashing, containing an isolated alkaline Bacillus protease according to claim 1.

5. A composition according to claim 4, comprising said alkaline Bacillus protease and at least one cleaning composition enzyme selected from the group consisting of other proteases, lipases, pectinases, amylases, nucleases, oxidoreductases and cellulases.

6. A composition according to claim 5, wherein said cleaning composition enzyme is a second protease.

7. A composition according to claim 4, comprising a combination of
   an alkaline Bacillus protease having the following properties:
   (1) Action: degradation of proteins and peptides;
   (2) pH optimum: approximately at pH values of 10.5 to 11.0;
   (3) pH stability: upon incubation at 4° C. for 24 hours at pH values of 9.7 to 10.8, the enzyme proves to be completely stable;
   (4) temperature optimum: approximately 60° C.;
   (5) temperature stability: by incubation of the protease at temperatures of up to 45° C. for 15 minutes, the activity of the protease is substantially 100%; after 15 minutes' incubation at 50° C., the residual activity of the protease is at least 90%, and
   an alkaline Bacillus protease having the following properties:
   (1) Action: degradation of proteins and
   (2) pH optimum: approximately at pH values of 8.5 to 9;
   pH stability: upon incubation at 4° C. for 24 hours at pH values of 5.5 to 10.5, the enzyme proves to be completely stable;
   (4) temperature optimum: approximately 50° C.;
   (5) temperature stability: by incubation of the protease at temperatures of up to 40° C. for 15 minutes, the activity of the protease is substantially 100%; after 15 minutes' incubation at 45° C., the residual activity of the protease is at least 95%.

8. A composition according to claim 4, comprising said alkaline Bacillus protease in a formulation for low use temperatures of up to about 60° C.

* * * * *